United States Patent
Suh

(10) Patent No.: US 7,481,811 B2
(45) Date of Patent: Jan. 27, 2009

(54) TRANSLATIONAL PLATE WITH SPRING BEAM RETAINER

(75) Inventor: Sean S. Suh, Plymouth Meeting, PA (US)

(73) Assignee: Synthes (U.S.A.), West Chester, PA (US)

( * ) Notice: Subject to any disclaimer, the term of this patent is extended or adjusted under 35 U.S.C. 154(b) by 175 days.

(21) Appl. No.: 11/078,803

(22) Filed: Mar. 11, 2005

(65) Prior Publication Data

US 2006/0217725 A1    Sep. 28, 2006

(51) Int. Cl.
*A61B 17/80* (2006.01)
(52) U.S. Cl. .................. 606/71; 606/289; 606/294; 606/295; 606/296
(58) Field of Classification Search ............. 606/69–71
See application file for complete search history.

(56) References Cited

U.S. PATENT DOCUMENTS

| 3,779,240 | A | * | 12/1973 | Kondo | 606/69 |
| 3,990,438 | A | * | 11/1976 | Pritchard | 606/73 |
| 6,258,089 | B1 | * | 7/2001 | Campbell et al. | 606/86 B |
| 6,413,259 | B1 | * | 7/2002 | Lyons et al. | 606/69 |
| 6,755,833 | B1 | | 6/2004 | Paul et al. | |
| 7,008,426 | B2 | * | 3/2006 | Paul | 606/70 |
| 7,025,769 | B1 | * | 4/2006 | Ferree | 606/69 |
| 2005/0192577 | A1 | | 9/2005 | Mosca et al. | |
| 2006/0229620 | A1 | * | 10/2006 | Rothman et al. | 606/69 |

FOREIGN PATENT DOCUMENTS

WO    WO 20006/047581 A    5/2006

\* cited by examiner

*Primary Examiner*—Eduardo C Robert
*Assistant Examiner*—Jerry Cumberledge
(74) *Attorney, Agent, or Firm*—Stroock & Stroock & Lavan LLP

(57) ABSTRACT

A fixation assembly is described, comprising a fixation plate having an upper surface, a lower surface, a longitudinal axis, and a first opening extending from the upper surface through to the lower surface; a first resilient element extending through at least a portion of the first opening; wherein the first opening is configured to receive a first bone fastener, the first bone fastener having a head and a shaft; wherein the first resilient element is deflectable from a first condition to a second condition; and wherein the first resilient element is configured to engage at least a portion of the head of the first bone fastener when the first bone fastener is at least partially inserted into the first opening. A method of use is also described.

1 Claim, 4 Drawing Sheets

TRANSLATIONAL PLATE WITH SPRING BEAM RETAINER

FIELD OF THE INVENTION

The present invention is related to a fixation system. More particularly, the invention is related to a fixation system with at least one spring beam retainer device for preventing fastener back-out.

BACKGROUND OF THE INVENTION

Orthopedic fixation devices such as plates are frequently coupled to bone with fasteners inserted through plate holes. It is known that securing such fasteners to the bone plate, for example through the use of expansion-head screws, can decrease the incidence of loosening of the fixation assembly post-operatively. It is also known that a bushing may be disposed in each plate hole to receive the fastener to permit polyaxial movement so that the fastener may be angulated at a surgeon-selected angle. However, polyaxial movement of fasteners through set plate hole locations only increases attachment alternatives of the fasteners themselves. The plate holes remain fixed in relation to each other and to the longitudinal axis of the plate.

Typically, a spinal fixation plate is applied to the anterior side of the affected vertebrae to span at least one affected disc space or vertebra (i.e. one in which at least a portion of the disc has been removed and a spinal fusion spacer has been inserted). The plate is fixed to the vertebrae using bone screws and acts to keep the vertebrae generally aligned during the initial period following fixation in which fusion of the spacer to the adjacent vertebrae occurs. The plate also acts to prevent the spacer from being expelled from the disc space during this initial period.

Where a spinal fusion spacer is implanted between a pair of vertebrae to be fused, the spacer rests on the endplates of the vertebrae. The outer circumference of the end plates comprises hard cortical bone and thus provides a the best surface upon which to seat the spacer. The center portion of the endplates comprises a thin cortical bone shell overlying a core of softer cancellous bone. Most, if not all, of the spacer contact surface, however, may be located in this center portion.

Subsequent to placement of the spacer, the surgeon typically compresses the disc space by pressing the adjacent vertebrae together. This compression ensures a good engagement between the spacer the endplates, increasing the chances that fusion will occur. Often in the period immediately following surgery, the spacer will subside slightly either into the under-portion of the endplates or due to graft resorption (in the case of allograft spacers).

Where a rigid fixation plate is used to connect the vertebrae, this subsidence may tend to shift more of the spinal load to the plate than is desirable. Such load shifting can also occur due to inaccuracies in installing the plate to the vertebrae. In extreme circumstances, this load shifting can result in non-fusion of the spacer to the vertebra, since firm compression between the spacer and the vertebrae is one factor contributing to successful fusion.

Accordingly, there exists a need for a fixation system which provides the desired support to the vertebrae to be fused, and which allows limited translation of the vertebrae with respect to at least a portion of the plate, thereby limiting the undesirable effects of load shielding by the plate due to graft subsidence caused by settling or normal forces experienced in the spinal column. Promoting fusion of the adjacent vertebrae is thus accomplished.

However, fasteners used with both rigid and translational plates have a tendency to back-out of their installed positions under the influence of force and movements of the spine. The back-out of the fasteners is undesirable, as the fixation assembly may shift post-operatively to an undesired location, or loosen to an undesirable level.

Therefore, there exists a need for a fastener retaining device that can be coupled to a translational plate for preventing screw back-out. There also exists a need for such a retainer device to be conveniently situated in or around the plate, so as not to interfere with the insertion and/or placement of fasteners. There further exists a need for a retainer device to be bendable and/or shiftable by a surgeon without the use of strenuous force.

SUMMARY OF THE INVENTION

A fixation assembly is described, comprising a fixation plate having an upper surface, a lower surface, a longitudinal axis, and a first opening extending from the upper surface through to the lower surface; a first resilient element extending through at least a portion of the first opening; wherein the first opening is configured to receive a first bone fastener, the first bone fastener having a head and a shaft; wherein the first resilient element is deflectable from a first condition to a second condition; and wherein the first resilient element is configured to engage at least a portion of the head of the first bone fastener when the first bone fastener is at least partially inserted into the first opening.

The first bone fastener may be allowed to translate within the first opening. The first bone fastener may be allowed to translate in situ. The first bone fastener may be allowed to translate when at least a portion of the first bone fastener is inserted into a bone segment.

The first opening may be a slot. The first resilient element may be substantially parallel to the longitudinal axis of the fixation plate when the first resilient element is in the first condition. The head of the first bone fastener may further comprise at least one slot, wherein the slot may be configured to engage at least a portion of the first resilient element.

The assembly may further comprise a second opening having a second resilient element extending though at least a portion of the second opening. The first opening may have a centerline, wherein the first resilient element may be fixed to the fixation plate at a first and a second location, and wherein the first and second locations may be substantially collinear with the centerline. The first resilient element may be substantially linear in the first condition, wherein the first resilient element may be bowed in the second condition.

A fixation assembly is also described, comprising a fixation plate having an upper surface, a lower surface, a longitudinal axis, and a first opening extending from the upper surface through to the lower surface; a first resilient element extending into at least a portion of the first opening, and fixed to the plate at a first location; wherein the first opening is configured to receive a first bone fastener; and wherein the first resilient element is configured to engage at least a portion of the first bone fastener to prevent fastener back-out while allowing the first bone fastener to translate within the first opening.

The first resilient element may be substantially parallel to the longitudinal axis of the fixation plate when the first resilient element is in the first condition.

The first bone fastener may further comprise a head, the head may have at least one slot, and wherein the slot may be configured to engage at least a portion of the first resilient element. The assembly may further comprise a second opening having a second resilient element extending though at least a portion of the second opening. The first opening may have a centerline, wherein the first resilient element may be further fixed to the fixation plate at a second location, and wherein the first and second locations may be substantially collinear with the centerline.

A method of preventing fastener back-out in a fixation assembly is also described, comprising the steps of: (a) providing a fixation plate having an upper surface, a lower surface, a longitudinal axis, and a first opening extending from the upper surface through to the lower surface; a first resilient element extending through at least a portion of the first opening, the first resilient element having a longitudinal axis; wherein the first bone fastener has a head and a shaft; and wherein the first resilient element is deflectable from a first condition to a second condition; (b) initially deflecting the first resilient element in a direction substantially transverse to the longitudinal axis of the first resilient element; and (c) inserting the first bone fastener through the first opening and into a bone segment; wherein the first bone fastener is inserted to a sufficient depth to allow the first resilient element to engage the head of the first bone fastener.

The first resilient element may be initially deflected by the shaft of the first bone fastener. The first resilient element may be initially deflected directly by a user.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE INVENTION

Figure 1:
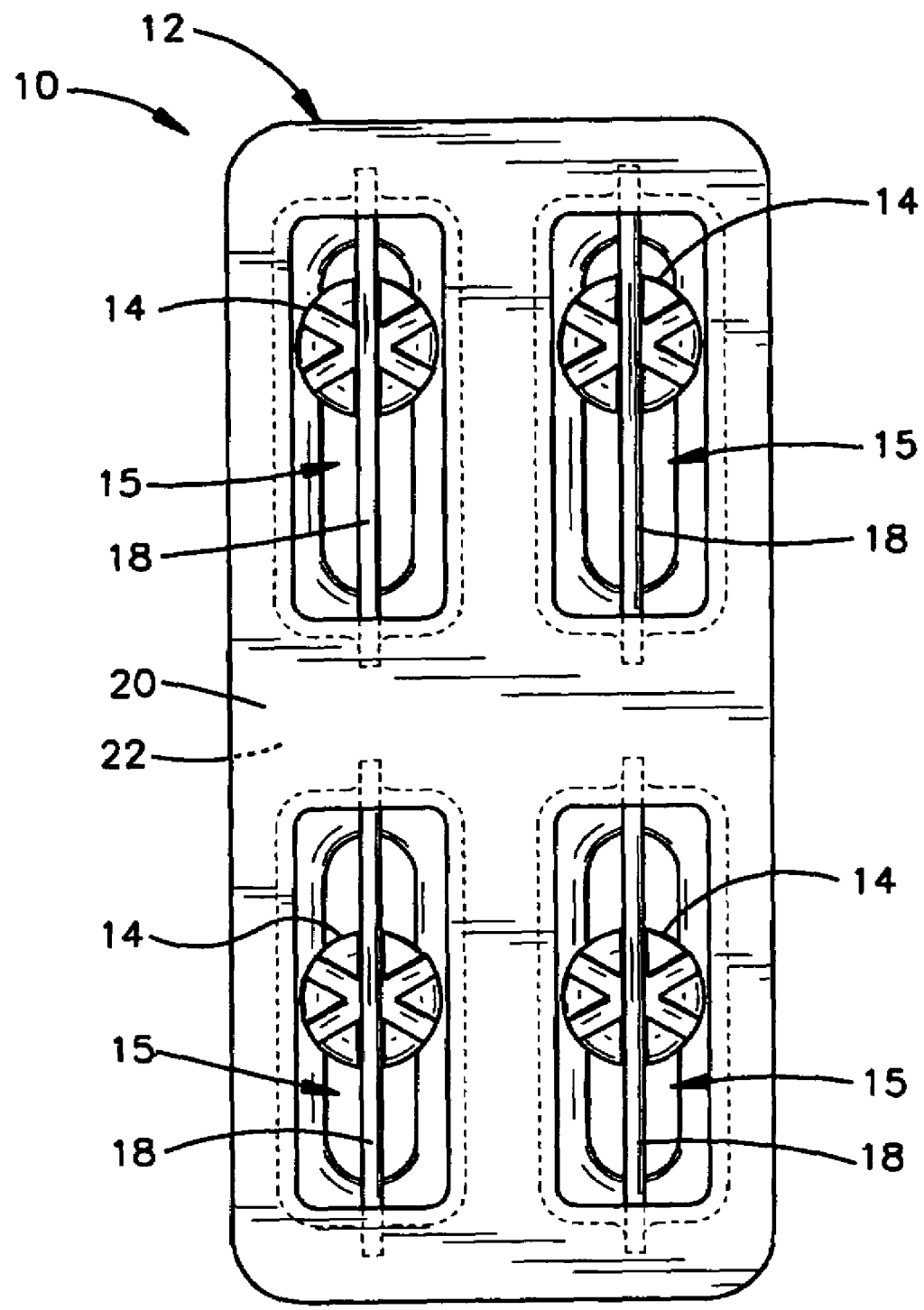
FIG. 1 is a top view of an embodiment of a one-level bone fixation assembly with fasteners and spring beam retainer devices.

The plates described herein may be used in spinal fusion procedures in which a damaged or diseased disc (or part of a disc) is removed from between a pair of vertebrae and a spinal fusion spacer is placed between the vertebrae. The plates may be applied to an anterior portion of the affected vertebrae to span the affected disc space, and may be fixed to the vertebrae using bone screws. The plate may function to maintain the vertebrae aligned during the initial period following fixation in which fusion of the spacer to the adjacent vertebrae occurs. The plate may also function to share some of the axial spinal load applied to the fusion spacer to prevent extreme subsidence of the spacer into the vertebral body, such as where the patient has poor bone quality. The plates may also act to prevent the spacer from being expelled from the disc space during the initial post-operative period.

The plates may be used for single level (i.e. one-disc) or multiple-level (i.e. multiple disc) fusion procedures. Some embodiments may be used for corpectomy procedures, in which at least a portion of a vertebral body is removed. Single level plates generally may have two pairs of bone screw holes, while the multi-level plates generally may have three or more pairs of holes.

FIGS. 1-7 shows a one-level bone fixation assembly 10. This embodiment includes a bone fixation plate 12 which, in this particular example, may be a spinal fixation plate. A plurality of fasteners 14 may extend through openings 15 in the plate 12. A plurality of spring beam retainer devices 18 may be coupled to the plate 12. The retainer devices 18 may engage the fasteners 14 to restrain them from rotating back outward from their installed positions when the screws 14 and the plate 12 are together mounted on the spine.

The plate 12 may be configured to overlie the a section of the spine to provide support that maintains the alignment of two or more vertebrae in that section of the spine. As shown in FIG. 1, this example of a plate 12 has a vertically elongated generally rectangular shape with rounded corners, and may have planar upper and lower side services 20 and 22. The thickness and material of the plate 12 may enable a surgeon to deflect it from a flat configuration as needed for the plate 12 to extend over the spine with an appropriate contour.

The openings 15 may be arranged in pairs at the first and second end portions of the plate 12. In this arrangement, the first pair of fasteners 14 at the first openings 15 can fasten the plate 12 to a first vertebra, and the second pair of fasteners 14 at the second openings 15 can fasten the plate 12 to a second vertebra beneath the first vertebra. Additionally, the openings 15 in at least one pair may be shaped as elongated slots. In this example, both pairs of openings 15 may be shaped as elongated slots. This may permit the first and second pairs of fasteners 14 to translatably move within the slots 15 when compression of the spine causes first and second vertebrae to move relatively toward each other lengthwise of the plate 12. Slots 15 may also be fitted with captive clips (not shown) to allow fasteners 14 to move within the slots 15 and further prevent fastener 14 back-out, the details, materials, and methods of which are described in U.S. patent application Ser. No. 10/653,164 entitled "Bone Plate with Captive Clips", by Duong, et al., filed Sep. 3, 2003, the entire disclosure of which application is expressly incorporated by reference herein.

Figure 2:
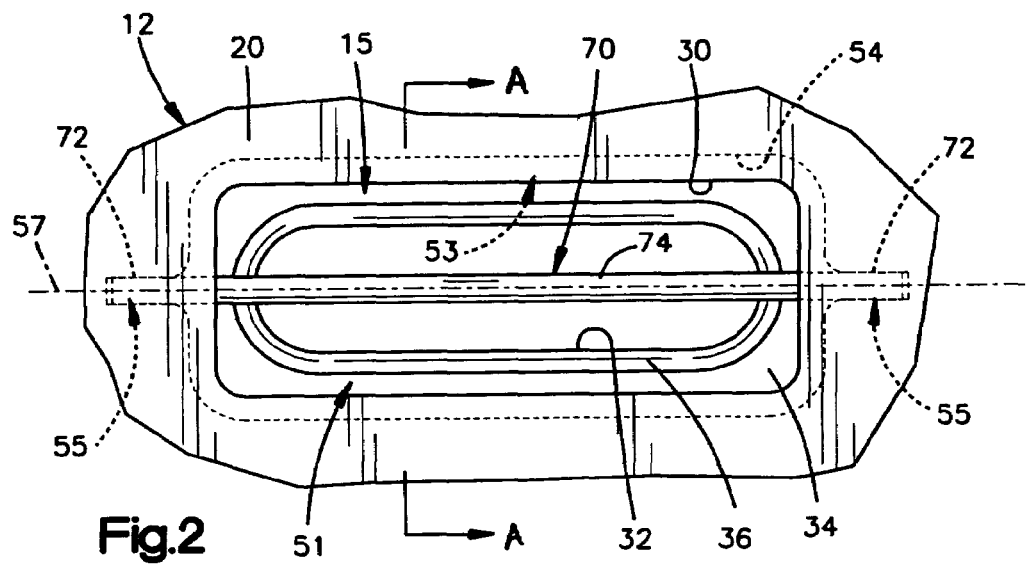
FIG. 2 is a partial enlarged top view of the assembly of FIG. 1 without a fastener, the spring beam retainer device in an unstressed, unengaged position.
Figure 3:
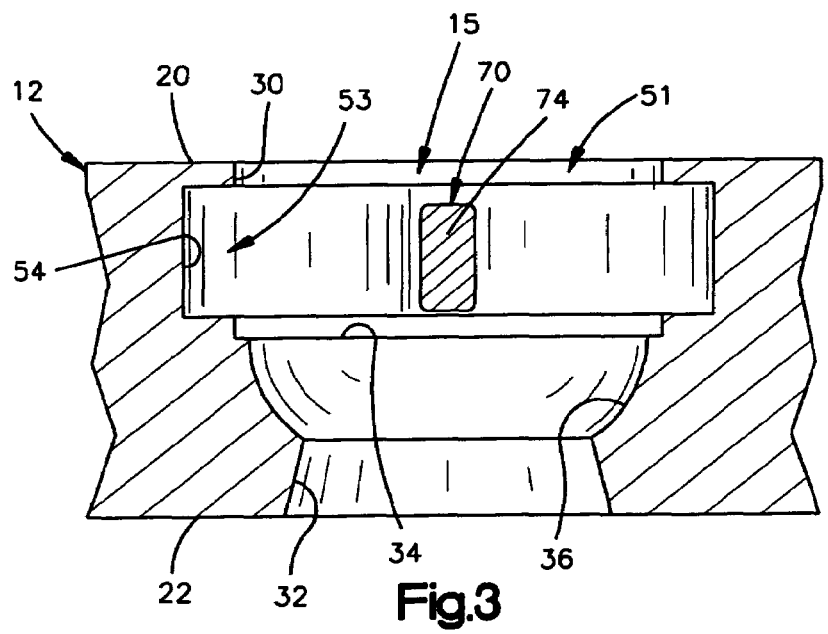
FIG. 3 is a partial cross-sectional view of the assembly of FIG. 2 taken on the line A-A.

It may be preferable to have each slot 15 of substantially the same dimension, size and shape. Each slot 15 may have the configuration as shown in FIGS. 2-3. Each slot 15 may thus defined by inner edge surfaces of the plate 12 that together extend through the plate 12 between the opposite side surfaces 20 and 22. A first inner edge surface 30 may provide the slot 15 with a substantially rectangular peripheral shape adjacent to the upper side surface 20 of the plate 12. A second inner edge surface 32 may provide the slot 15 with a generally shorter and narrower shape, with rounded opposite ends, adjacent to the lower side surface 22. A first shoulder surface 34 may have a planar contour facing upward within the slot 15. A second shoulder surface 36 may be located between the first shoulder surface 34 and the second inner edge surface 32. That shoulder surface 36 may also face upward, but may have a contour with an generally arcuate profile, as shown in FIG. 3.

Figure 4:
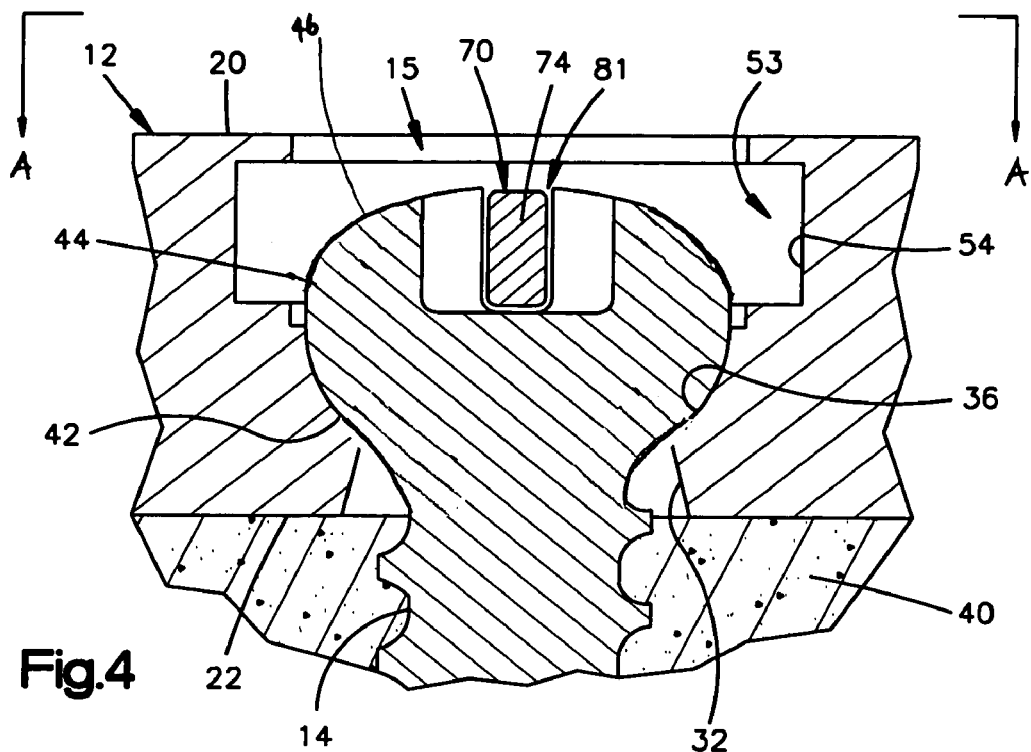
FIG. 4 is a partial cross-sectional view of the assembly of FIG. 2 taken on the line A-A, with a fastener engaging a spring beam retainer device and implanted into a vertebra.

Thus, slot 15 may be configured to provide a path of movement along which a fastener 14 is movable into and back outward from an installed position in which the fastener 14 fastens the plate 12 to a vertebra 40, as shown in FIG. 4. As the fastener 14 is being tightened into this position, an arcuate lower surface 42 of the fastener head 44 may become seated against the arcuate inner edge surface 36 within the slot 15. It may be preferable for the entire fastener head 44 to be located within the slot 15 between the upper and lower side surfaces 20 and 22 of the plate 12.

As further shown in FIGS. 2-3, a generally shaped region 51 of the slot 15 may be located above the planar shoulder surface 34. The shaped region 51 may be bounded by the first inner edge surface 30. An inner peripheral region 53 of the slot 15 may surround the shaped region 51. The inner peripheral region 53 may be bounded by an inner edge surface 54 that may be recessed from the first inner edge surface 30 around the entire length of the first inner edge surface 30. As shown in FIG. 2, the recessed inner edge surface 54 may define opposite end portions 55 of the inner peripheral region 53. Those portions 55 may be configured as bores that extend oppositely along the longitudinal centerline 57 of the slot 15.

Figure 5:
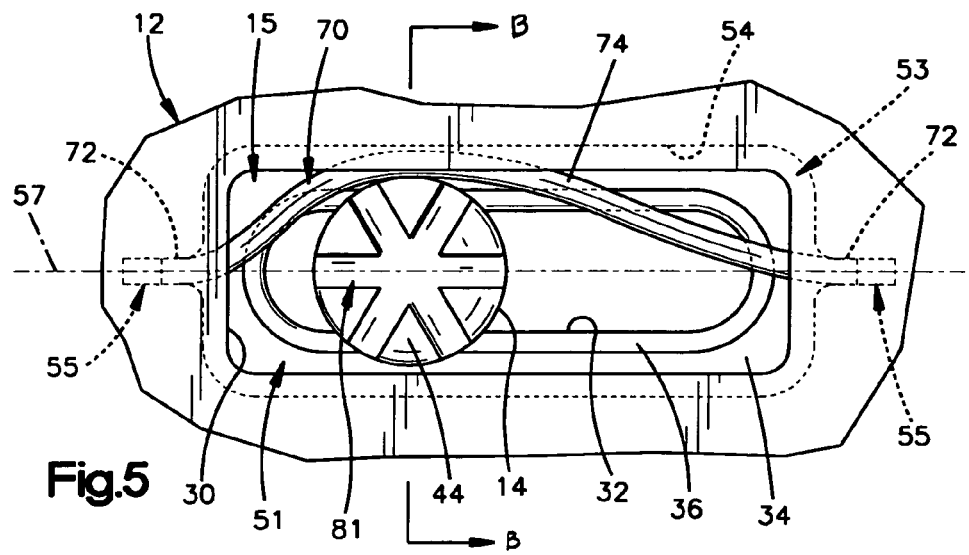
FIG. 5 is a partial enlarged top view of the assembly of FIG. 1 with a fastener, the spring beam retainer device in an stressed, unengaged position.
Figure 6:
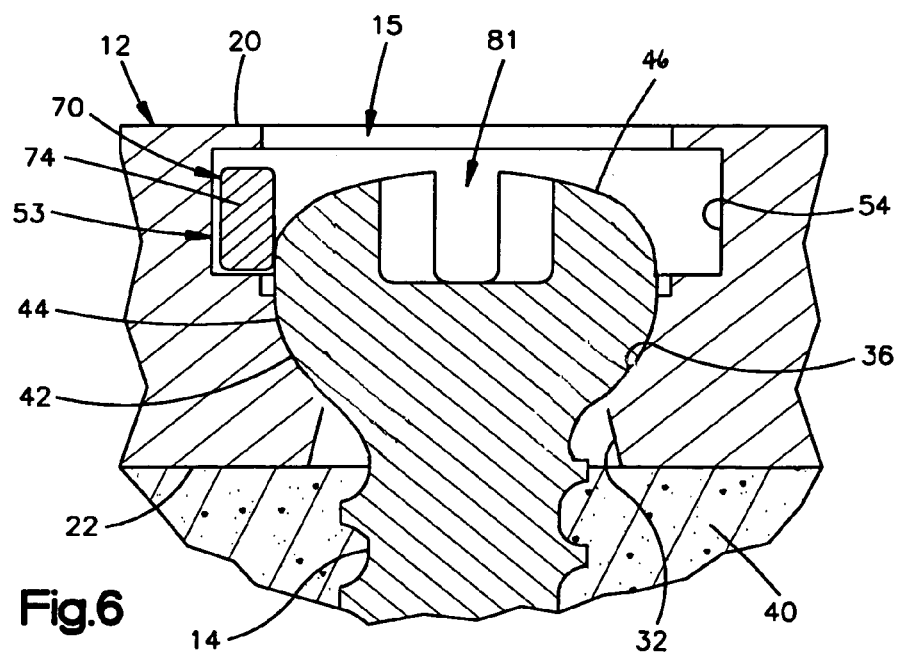
FIG. 6 is a partial cross-sectional view of the assembly of FIG. 5 taken along the line B-B.

It may also be preferable for the spring beam retainer devices 18 to be similarly dimensioned, sized, and shaped, as shown in FIGS. 2-3. In this particular example, each spring-loaded retainer device 18 takes the form of a wire spring 70. The spring 70 may be shaped as a bar having a generally rectangular cross-section, with rounded corners, substantially uniform along its length. Opposite end portions 72 of the spring 70 may be received closely within the bores 55 to slide longitudinally within the bores 55. The spring 70 may thus be mounted on the plate 12 to be shifted from a first, unstressed, unengaged condition, as shown in FIG. 2, to a second, stressed, unengaged condition, as shown in FIG. 5, under an applied force, and to rebound from the second condition to either a third, unstressed, engaged condition (if fastener 14 is present), or back to the first, unstressed unengaged condition (if no fastener 14 is present) upon release of the applied force.

In this embodiment, the first condition (see FIG. 2) of the spring 70 is an unstressed, unengaged rest condition. In this first condition, intermediate portion 74 of the spring 70 may extend longitudinally between the opposite end portions 72 in a linear configuration centered on the longitudinal centerline 55 of the slot 15. The second condition (see FIG. 5) of the spring 70 is a stressed, unengaged condition in which the intermediate portion 74 may be bowed between the opposite end portions 72, which then may be drawn slightly outward from their rest positions within the bores 55. Accordingly, when the spring 70 is in the first condition, the intermediate portion 74 of the spring 70 may extend into the path of movement that the fastener 14 may take through the slot 15 toward and into its installed position as it is being implanted into a vertebra 40. When the spring 70 is in the second condition, it is generally located outside the path of movement of the fastener 14.

In use, the spring 70 may be urged from the first condition to the second condition by the lower arcuate surface 42 of the fastener 14 as the fastener is lowered into the slot 15. Initially, the spring 70 may be pushed to one side or the other of the fastener 14, as the fastener is introduced into the slot 15. This initial push may be achieved by the surgeon using his or her hand (or a tool) to deflect the spring 70 in a desired direction. As the fastener 14 proceeds further into the slot 15, and the screw head engages the spring 70, the lower arcuate surface 42 may urge the spring 70 into a recessed inner peripheral region 53 of a slot 15.

After engaging a lower arcuate surface 42 of a fastener 14, the spring 70 may engage an upper arcuate surface 46 as the fastener 14 is further introduced into slot 15. The spring 70 may remain in a recessed inner peripheral region 53 until the resilient restoring force attempting to return the spring 70 to the unstressed position is sufficient to overcome the axial force provided by the fastener head 44. An example of this scenario is seen, just before spring 70 returns to an unstressed condition, in FIG. 6. The relationship between the magnitude and/or direction of the resilient force of spring 70 and axial force provided by fastener head 44 is at least in part determined by the shape of the lower and upper arcuate surfaces 42, 46, and the cross-sectional shape and/or surface features of the spring 70.

Figure 7:
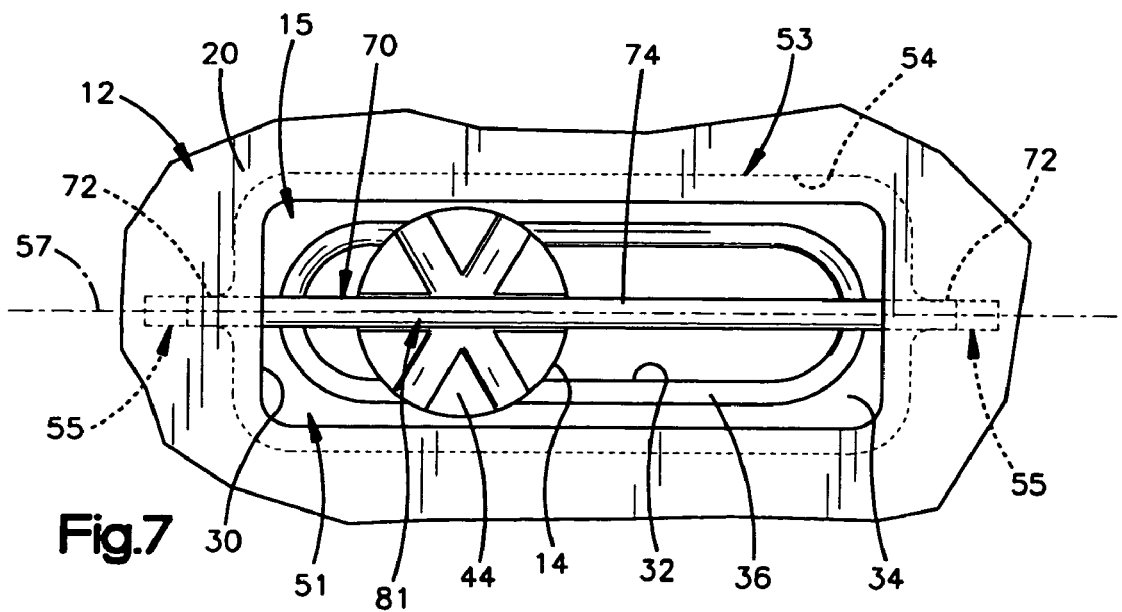
FIG. 7 is a partial enlarged top view of the assembly of FIG. 1 with a fastener, the spring beam retainer device in an unstressed, engaged position.

Once spring 70 is able to shift back toward the unstressed condition, it may slide and/or rotate over at least a portion of the upper arcuate surface 46 of fastener head 44, and ultimately may settle in a driving tool slot 81 of fastener head 44. As stated above, spring 70 may be situated in a third, unstressed condition when a fastener 14 is inserted into slot 15. Spring 70 may rest either completely or partially in driving tool slot 81 while in the third condition, and may block the fastener 14 from rotating relative to the plate 12, as shown in FIGS. 4 and 7. This may restrain the fastener 14 from backing out of the installed position in which it has been implanted into a vertebra 40. However, the engagement of the spring 70 (in a third condition) with a fastener head 44 generally should not interfere with the ability of fastener 14 to translate within a slot 15, while the fastener 14 is inserted into a vertebrae 40 and/or in situ.

Spring 70, while shown in a generally rectangular cross-sectional shape, may be a variety of shapes and/or sizes. For instance, spring 70 may have a circular, elliptical, square, triangular, or other polygonal cross-sectional shape. The cross-sectional shape of spring 70 may also vary along the length of the spring. At least a portion of the spring 70 should have a shape and/or size that is appropriate for at least a partial insertion into a chosen driving tool slot 81 of a fastener 14.

Moreover, spring 70 may also have a variety of surface textures and finishes. Spring 70 may be relatively smooth, or may instead have serrations, grooves, or other surface features on at least a portion of the outer surface of spring 70. Furthermore, spring 70 may be of uni-body construction, or instead may be comprised of a plurality of layers.

The sizes, dimensions, and shapes of each of the above described fixation plates and other fixation assembly components may be varied to fit the anatomy of a given patient, depending at least in part on the size of the vertebra the plates will be attached to, and the size of the intervertebral space to be spanned. Fixation assemblies may also be substantially flat, to reduce the overall profile of the assemblies.

It is also expressly contemplated that each of the above described fixation assemblies may be assembled in a multi-level arrangement to span more than one intervertebral disc space. It is also contemplated that each of the above described assemblies may be assembled in corpectomy model, to span the length of at least one removed vertebral body. Variations or combinations of these alternatives are also contemplated.

Each of the fasteners, fixation plates, fastener retainers, and other components disclosed herein may be formed of a titanium alloy such as titanium-aluminum-niobium, which may be anodized. One material for use with each of the plates and screws described herein is Ti-6Al-7Nb, with a density of about 4.52 gm/cc, a modulus of elasticity of about 105 GPa, an ultimate tensile strength of about 900 MPa, and a yield strength of about 800 MPa. Surfaces of the fasteners may also be burr free, with all sharp edges broken to a maximum of 0.1 mm. Spring 70 may be made of any biocompatible, resilient material, including elgiloy and nitinol.

It should be noted that the aforementioned descriptions and illustrations have been provided as examples of the configurations of translation plates that may be designed and assembled using the principles of the invention. These examples will be understood to one of ordinary skill in the art as being non-limiting in that a fixation assembly employing one or more of the disclosed features may be produced as desired or required for a particular patient's need. Thus, the features disclosed are "modular" in nature.

This written description sets forth the best mode of the claimed invention, and describes the claimed invention to enable a person of ordinary skill in the art to make and use it, by presenting examples of the elements recited in the claims. The patentable scope of the invention is defined by the claims themselves, and may include other examples that occur to those skilled in the art. Such other examples, which may be available either before or after the application filing date, are intended to be within the scope of the claims if they have structural elements that do not differ from the literal language of the claims, or if they include equivalent structural elements with insubstantial differences from the literal language of the claims.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

The invention claimed is:

1. A fixation plate comprising:

an upper surface, a lower surface, a longitudinal axis, and an elongated slot, the elongated slot extending from said upper surface to said lower surface, the elongated slot including a first end, a second end, a first side, a second side and a centerline; first and second inner peripheral regions formed in the fixation plate adjacent the first and second sides of the elongated slot respectively; a first blind bore formed in the plate adjacent the first end of the slot and a second blind bore formed in the plate adjacent to the second end of the slot, wherein the first and second blind bores are substantially collinear with the centerline of the slot; and a resilient element having a first end, a second end and an intermediate portion, the resilient element extending across at least a portion of the elongated slot, wherein the intermediate portion of said resilient element is deflectable from a first condition wherein the resilient element is received within one of the first and second inner peripheral regions to a second condition wherein the resilient element is configured to overlay at least a portion of a head of a bone screw when the head of the bone screw is at least partially inserted into said elongated slot;

wherein the first end of the resilient element is slidably received within the first blind bore and the second end of the resilient element is slidably received within the second blind bore, the elongated slot is configured to receive at least one bone fixation element so that said fixation element is permitted to translate within said slot in a direction substantially parallel to the longitudinal axis of the fixation plate, and the bone fixation element includes a head region having a groove formed thereon and a shank region, the resilient element being seated within the groove formed in the head of the bone screw when said bone screw is at least partially inserted into said elongated slot.

* * * * *